United States Patent [19]

Goeddel et al.

[11] Patent Number: 4,634,677

[45] Date of Patent: Jan. 6, 1987

[54] PLASMID CAPABLE OF EXPRESSING HUMAN GROWTH HORMONE

[75] Inventors: David V. Goeddel; Herbert L. Heyneker, both of Burlingame, Calif.

[73] Assignee: Genentech, Inc., South San Francisco, Calif.

[21] Appl. No.: 296,099

[22] Filed: Aug. 26, 1981

Related U.S. Application Data

[62] Division of Ser. No. 55,126, Jul. 5, 1979, Pat. No. 4,342,832.

[51] Int. Cl.$^4$ .................. C12N 1/00; C12N 15/00
[52] U.S. Cl. .................. 435/317; 435/172.3; 935/9; 935/29; 935/13
[58] Field of Search .................. 435/172, 68, 317, 70, 435/71

[56] References Cited

U.S. PATENT DOCUMENTS

| | | |
|---|---|---|
| 4,190,495 | 2/1980 | Curtiss, III . |
| 4,237,224 | 12/1980 | Cohen . |
| 4,332,892 | 6/1982 | Ptashne et al. ............. 435/172 |
| 4,342,832 | 8/1982 | Goeddel . |
| 4,356,270 | 10/1982 | Itakura et al. ............. 435/172.3 |
| 4,363,877 | 12/1982 | Goodman et al. .......... 435/172.3 |

FOREIGN PATENT DOCUMENTS

| | | |
|---|---|---|
| 0006694 | 1/1980 | European Pat. Off. . |
| 0009930 | 4/1980 | European Pat. Off. . |
| 0020251 | 12/1980 | European Pat. Off. . |
| 0020147 | 12/1980 | European Pat. Off. . |
| 0026598 | 4/1981 | European Pat. Off. . |

OTHER PUBLICATIONS

Li et al., J. Am. Chem. Soc., vol. 92, pp. 7608 & 7609, (1970).
Roberts et al., Proc. Natl. Acad. Sci. USA, vol. 76, No. 2, pp. 760–764, (Feb. 1979).
Mantial et al., Science, vol. 205, pp. 602–607, Aug. 1979.
Itakura et al., Science, vol. 198, pp. 1056–1063, Dec. 1977.
Backman et al., Cell, vol. 13 pp. 65–71, Jan. 1978.
Bolivar et al., Gene 2, pp. 95–113 (1977).
Chang et al., Nature, vol. 275, pp. 617–624 (Oct. 1978).
Crea et al., PNAS, vol. 75, pp. 5765–5769 (Dec. 1978).
Curtis et al., Molecular Cloning of Recombinant DNA, by Scott et al., pp. 99–111 (1977).
Goeddel et al., PNAS, vol. 76, pp. 106–110 (1979).
Goeddel et al., Nature, vol. 281, pp. 544–548 (Oct. 1979).
Humphries et al., Nucleic Acids Res., 4(7) pp. 2389–2406 (1977).
Klenow et al., PNAS, vol. 65, pp. 168–175 (Jan. 1970).
Kornberg, DNA Synthesis, pp. 87–88, pub. by W. H. Freeman & Co. (1974).
Marians et al., Nature, vol. 263, pp. 744–748 (Oct. 1976).
Maxam et al., PNAS, vol. 74, pp. 560–564 (Feb. 1977).
Newmark, Nature, vol. 280, pp. 637–638 (Aug. 23, 1979).
Polisky et al., PNAS, vol. 73:11, pp. 3900–3904 (1976).
Razin et al., PNAS, vol. 75, pp. 4268–4270 (Sep. 1978).
Seeburg et al., Nature, vol. 276, pp. 795–798 (Dec. 1978).
Shine et al., Nature, vol. 285, pp. 456–461 (Jun. 12, 1980).
Sutcliff, Cold Spring Harbor Symposium 43, pp. 70–90 (1978).
Ullrich et al., Science, vol. 196, pp. 1313–1319 (1977).
Villa-Komaroff et al., PNAS, vol. 75, pp. 3727–3731 (Aug. 1978).
Wickens et al., The Journal of Biological Chemistry, vol. 253, No. 7, pp. 2483–2495 (1978).
Chemical Abstracts vol. 88, p. 249, No. 101458c (Apr. 1978).
Chemical Abstracts vol. 87, No. 114458g.
The Economist, pp. 87–88 (Jul. 14, 1979).
Technology Review, pp. 12 & 13, Dec. 1976.
Time, Jul. 30, 1970, p. 70.
Merck Index, 9th Edition 7290 (1976).

Primary Examiner—Alvin E. Tanenholtz

[57] ABSTRACT

Described are methods and means for the construction and microbial expression of quasi-synthetic genes arising from the combination of organic synthesis and enzymatic reverse transcription from messenger RNA sequences incomplete from the standpoint of the desired protein product. Preferred products of expression lack bio-inactivating leader sequences common in eukaryotic expression products but problematic with regard to microbial cleavage to yield bioactive material. Illustrative is a preferred embodiment in which a gene coding for human growth hormone (useful in, e.g., treatment of hypopituitary dwarfism) is constructed and expressed.

7 Claims, 5 Drawing Figures

HGH (1-24)

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|--|--|--|--|--|--|--|--|--|--|--|--|--|--|--|--|--|--|--|--|--|--|--|--|--|
|  | fmet | Phe | Pro | Thr | Ile | Pro | Leu | Ser | Arg | Leu | Phe | Asp | Asn | Ala | Met | Leu | Arg | Ala | His | Arg | Leu | His | Gln | Leu | Ala |

EcoRI — U$_1$ — U$_2$ — U$_3$ — U$_4$ — U$_5$ — U$_6$ —

AATTCTATGTTTCCCAACTATACCACTATCTCGTCTATTCGATAAACGCTATGCTTCGTGCTCTTCGTCTTCATCAGCTGCCTA

GATACAAAGGGTTGATATGGTGATAGAGCAGATAAGCTATTTGCGATACGAAGCACGAGAAGCAGAAGTAGTCGACGGATTCGA

L$_6$ — L$_5$ — L$_4$ — L$_3$ — L$_2$ — L$_1$ —

Hae III    Hind III

FIG. 1.

```
                  24
                  Ala Phe Asp Thr Tyr Gln Glu Phe Glu Ala Tyr Ile Pro Lys Glu Gln Lys Tyr Ser Phe Leu Gln Asn Pro Gln Thr Ser
5'...G            GCC UUU GAC ACC UAC CAG GAG UUU GAA GCC UAU AUC CCA AAG GAA CAG AAG UAU UCA UUC CUG CAG AAC CCC CAG ACC UCC
                                                                                                          Pst I
                                                40                                                                   80

Leu Cys Phe Ser Glu Ser Ile Pro Thr Pro Ser Asn Arg Glu Glu Thr Gln Gln Lys Ser Asn Leu Glu Leu Leu Arg Ile Ser Leu Leu
CUC UGU UUC UCA GAG UCU AUU CCG ACA CCC UCC AAC AGG GAG GAA ACA CAA CAG AAA UCC AAC CUA GAG CUG CUC CGC AUC UCC CUG CUG

Leu Ile Gln Ser Trp Leu Glu Pro Val Gln Phe Leu Arg Ser Val Phe Ala Asn Ser Leu Val Tyr Gly Ala Ser Asp Ser Asn Val Tyr
CUC AUC CAG UCG UGG CUG GAG CCC GUG CAG UUC CUC AGG AGU GUC UUC GCC AAC AGC CUA GUG UAC GGC GCC UCU GAC AGC AAC GUC UAU
                                                            100                                                       140

Asp Leu Lys Asp Leu Glu Glu Gly Ile Gln Thr Leu Met Gly Arg Leu Glu Asp Gly Ser Pro Arg Thr Gly Gln Ile Phe Lys Gln
GAC CUC AAG GAC CUA GAG GAA GGC AUC CAA ACG CUG AUG GGG AGG CUG GAA GAU GGC AGC CCC CGG ACU GGG CAG AUC UUC AAG CAG
                                                                                                              Bgl II

Thr Tyr Ser Lys Phe Asp Thr Asn Ser His Asn Asp Ala Leu Leu Lys Asn Tyr Gly Leu Leu Tyr Cys Phe Arg Lys Asp Met Asp
ACC UAC AGC AAG UUC GAC ACA AAC UCA CAC AAC GAU GCC CUA CUC AAG AAC UAC GGG CUG CUC UAC UGC UUC AGG AAG GAC AUG GAC
                                                160                                                       191

Lys Val Glu Thr Phe Leu Arg Ile Val Gln Cys Arg Ser Val Glu Gly Ser Cys Gly Phe Stop
AAG GUC GAG ACA UUC CUG CGC AUC GUG CAG UGC CGC UCU GUG GAG GGC AGC UGU GGC UUC UAG  CUGCCCGGGGUGGCAUCCCUGACCCUCCCCAGU
                                                            Pvu II                                          Sma I
                                                                                                            Xma I
                                    180

GCCUCUCCUGGCC....3'
    Hae III
```

FIG. 3.

PLASMID CAPABLE OF EXPRESSING HUMAN GROWTH HORMONE

This is a division of application Ser. No. 055,126 filed July 5, 1979 now U.S. Pat. No. 4,342,832.

BACKGROUND OF THE INVENTION

Genetic Expression

The DNA (deoxyribonucleic acid) of which genes are made comprises both protein-encoding or "structural" genes and control regions that mediate the expression of their information through provision of sites for RNA polymerase binding, information for ribosomal binding sites, etc. Encoded protein is "expressed" from its corresponding DNA by a multistep process within an organism by which:

1. The enzyme RNA polymerase is activitated in the control region (hereafter the "promoter") and travels along the structural gene, transcribing its encoded information into messenger ribonucleic acid (mRNA) until transcription of translatable mRNA is ended at one or more "stop" codons.

2. The mRNA message is translated at the ribosomes into a protein for whose amino acid sequence the gene encodes, beginning at a translation "start" signal, most commonly ATG (which is transcribed "AUG" and translated "f-methionine").

In accordance with the genetic code, DNA specifies each amino acid by a triplet or "codon" of three adjacent nucleotides individually chosen from adenosine, thymidine, cytidine and guanine or, as used herein, A,T,C, or G. These appear in the coding strand or coding sequence of double-stranded ("duplex") DNA, whose remaining or "complementary" strand is formed of nucleotides ("bases") which hydrogen bond to their complements in the coding strand. A complements T, and C complements G. These and other subjects relating to the background of the invention are discussed at length in Benjamin Lewin, *Gene Expression* 1, 2 (1974) and 3 (1977), John Wiley and Sons, N.Y. This and the other publications alluded to herein are incorporated by reference.

DNA Cleavage and Ligation

A variety of techniques are available for DNA recombination, according to which adjoining ends of separate DNA fragments are tailored in one way or another to facilitate ligation. The latter term refers to the formation of phosphodiester bonds between adjoining nucleotides, most often through the agency of the enzyme T4 DNA ligase. Thus, blunt ends may be directly ligated. Alternatively, fragments containing complementary single strands at their adjoining ends are advantaged by hydrogen bonding which positions the respective ends for subsequent ligation. Such single strands, referred to as cohesive termini, may be formed by the addition of nucleotides to blunt ends using terminal transferase, and sometimes simply by chewing back one strand of a blunt end with an enzyme such λ-exonuclease. Again, and most commonly, resort may be had to restriction endonucleases (hereafter, "restriction enzymes"), which cleave phosphodiester bonds in and around unique sequences of nucleotides of about 4–6 base pairs in length ("rest iction sites"). Many restriction enzymes and their recognition sites are known. See, e.g., R. J. Roberts, *CRC Critical Reviews in Biochemistry*, 123 (November 1976). Many make staggered cuts that generate short complementary single-stranded sequences at the ends of the duplex fragments. As complementary sequences, the protruding or "cohesive" ends can recombine by base pairing. When two different molecules are cleaved with this enzyme, crosswise pairing of the complementary single strands generates a new DNA molecule, which can be given covalent integrity by using ligase to seal the single strand breaks that remain at the point of annealing. Restriction enzymes which leave coterminal or "blunt" ends on duplex DNA that has been cleaved permit recombination via, e.g., T4 ligase with other blunt-ended sequences.

Cloning Vehicles and Recombinant DNA

The present purposes, a "cloning vehicle" is an extrachromosomal length of duplex DNA comprising an intact replicon such that the vehicle can be replicated when placed within a unicellular organism ("microbe") by transformation. An organism so transformed is called a "transformant". Presently, the cloning vehicles commonly in use are derived from viruses and bacteria and most commonly are loops of bacteria DNA called "plasmids".

Advances in biochemistry in recent years have led to the construction of "recombinant" cloning vehicles in which, for example, plasmids are made to contain exogenous DNA. In particular instances the recombinant may include "heterologous" DNA, by which is meant DNA that codes for polypeptides oridinarily not produced by the organism susceptible to transformation by the recombinant vehicle. Thus, plasmids are cleaved with restriction enzymes to provide linear DNA having ligatable termini. These are bound to an exogenous gene having ligatable terminal to provide a biologically functional moiety with an intact replicon and a phenotypical property useful in selecting transformants. The recombinant moiety is inserted into a microorganism by transformation and the transformant is isolated and cloned, with the object of obtaining large populations that include copies of the exogenous gene and, in particular cases, with the further object of expressing the protein for which the gene codes. The associated technology and its potential applications are reviewed in extenso in the Miles International Symposium Series 10: *Recombinant Molecules: Impact on Science and Society*, Beers and Bosseff, eds., Raven Press, N.Y. (1977).

Recombinant DNA Expression

Aside from the use of cloning vehicles to increase the supply of genes by replication, there have been attempts, some successful, to actually express proteins for which the genes code. In the first such instance a gene for the brain hormone somatostation under the influence of the lac promotor was expressed in *E. Coli* bacteria. K. Itakura et al, *Science* 198, 1056 (1977). More recently, the A and B chains of human insulin were expressed in the same fashion and combined to form the hormone. D. V. Goeddel et al., *Proc. Nat'l. Acad. Sci., USA* 76, 106 (1979). In each case the genes were constructed in their entirety by synthesis. In each case, proteolytic enzymes within the cell would apparently degrade the desired product, necessitating its production in conjugated form, i.e., in tandem with another protein which protected it by compartmentalization and which could be extracellulary cleaved away to yield the product intended. This work is described in the following published British patent specifications of the assignee of the present application: GB No. 2007 675 A; GB No. 2 007 670 A; GB No. 2 007 676 A; and GB No. 2 008 123 A.

While the synthetic gene approach has proven useful in the several cases thus far discussed, real difficulties arise in the case of far larger protein products, e.g., growth hormone, interferon, etc., whose genes are correspondingly more complex and less susceptible to facile synthesis. At the same time, it would be desirable to express such products unaccompanied by conjugate protein, the necessity of whose expression requires diversion of resorces within the organism better committed to construction of the intended product.

Other workers have attempted to express genes derived not by organic synthesis but rather by reverse transcription from the corresponding messenger RNA purified from tissue. Two problems have attended this approach. To begin with, reverse transcriptase may stop transcription from mRNA short of completing cDNA for the entire amino acid sequence desired. Thus, for example, Villa-Komaroff et al obtained cDNA for rat proinsulin which lacked codons for the first three amino acids of the insulin precursor. *Proc. Nat'l. Acad. Sci., USA* 75 3727 (1978). Again, reverse transcription of mRNA for polypeptides that are expressed in precursor form has yielded cDNA for the precursor form rather than the bioactive protein that results when, in a eukaryotic cell, leader sequences are enzymatically removed. Thus far, no bacterial cell has been shown to share that capability, so that mRNA transcripts have yielded expression products containing the leader sequences of the precursor form rather than the bioactive protein itself. Villa-Komaroff, supra (rat proinsulin); P. H. Seeburg et al, *Nature* 276, 795 (1978) (rat pregrowth hormone).

Finally, past attempts by others to bacterially express hormones (or their precursors) from mRNA transcripts have on occasion led only to the production of conjugated proteins not apparently amenable to extra-cellular cleavage, e.g., Villa-Komaroff, supra, (penicillinase-proinsulin); Seeburg, supra (beta-lactamase-pregrowth hormone).

Human Growth Hormone

Human growth hormone ("HGH") is secreted in the human pituitary. It consists of 191 amino acids and, with its molecular weight of about 21,500, is more than three times as large as insulin. Until the present invention, human growth hormone could be obtained only by laborious extraction from a limited source—the pituitary glands of human cadavers. The consequent scarcity of the substance has limited its applications to the treatment of hypopituitary dwarfism, and even here reliable estimates suggest that human-derived HGH is available in sufficient quantity to serve not more than about 50% of afflicted subjects.

In summary, a need has existed for new methods of producing HGH and other polypeptide products in quantity, and that need has been particularly acute in the case of polypeptides too large to admit of organic synthesis or convenient synthesis of genes from which the peptide could be expressed. Expression of mammalian hormones from mRNA transcripts has offered the promise of side-stepping difficulties that attend the synthetic approach, but until the present has permitted only microbial production of bio-inactive conjugates from which the desired hormone could not practicably be cleaved.

SUMMARY OF THE INVENTION

The present invention provides methods and means for expressing quasi-synthetic genes wherein reverse transcription provides a substantial portion, preferably a majority, of the coding sequence without laborious resort to entirely synthetic construction, while synthesis of the remainder of the coding sequence affords a completed gene capable of expressing the desired polypeptide unaccompanied by bio-inactivating leader sequences or other extraneous protein. Alternatively, the synthetic remainder may yield a proteolysis-resistant conjugate so engineered as to permit extra-cellular cleavage of extraneous protein, yielding the bioactive form. The invention accordingly makes available methods and means for microbial production of numerous materials hitherto produced only in limited quantity by costly extraction from tissue, and still others previously incapable of industrial manufacture. In its most preferred embodiment the invention represents the first occasion in which a medically significant polypeptide hormone (human growth hormone) has been bacterially expressed while avoiding both intracellular proteolysis and the necessity of compartmentalizing the bioactive form in extraneous protein pending extracellular cleavage. Microbial sources for human growth hormone made available by the invention offer, for the first time, ample supplies of the hormone for treatment of hypopituitary dwarfism, together with other applications heretofore beyond the capacity of tissue-derived hormone sources, including diffuse gastric bleeding, pseudarthrosis, burn therapy, wound healing, dystrophy and bone knitting.

The manner in which these and other objects and advantages of the invention may be obtained will appear more fully from the detailed description which follows, and from the accompanying drawings relating to a preferred embodiment of the invention, in which:

FIG. 1 depicts the synthetic scheme for construction of a gene fragment coding for the first 24 amino acids of human growth hormone, together with the start signal ATG and linkers used in cloning. The arrows in the coding or upper strand ("U") and in the complementary or lower strand ("L") indicate the oligonucleotides joined to form the depicted fragment;

FIG. 3 illustrates the DNA sequence (coding strand only) of the Hae III restriction enzyme fragment of a pituitary mRNA transcript, with the numbered amino acids of human growth hormone for which they code. Key restriction sites are indicated, as is DNA (following "stop") for untranslated mRNA;

Figure 2:
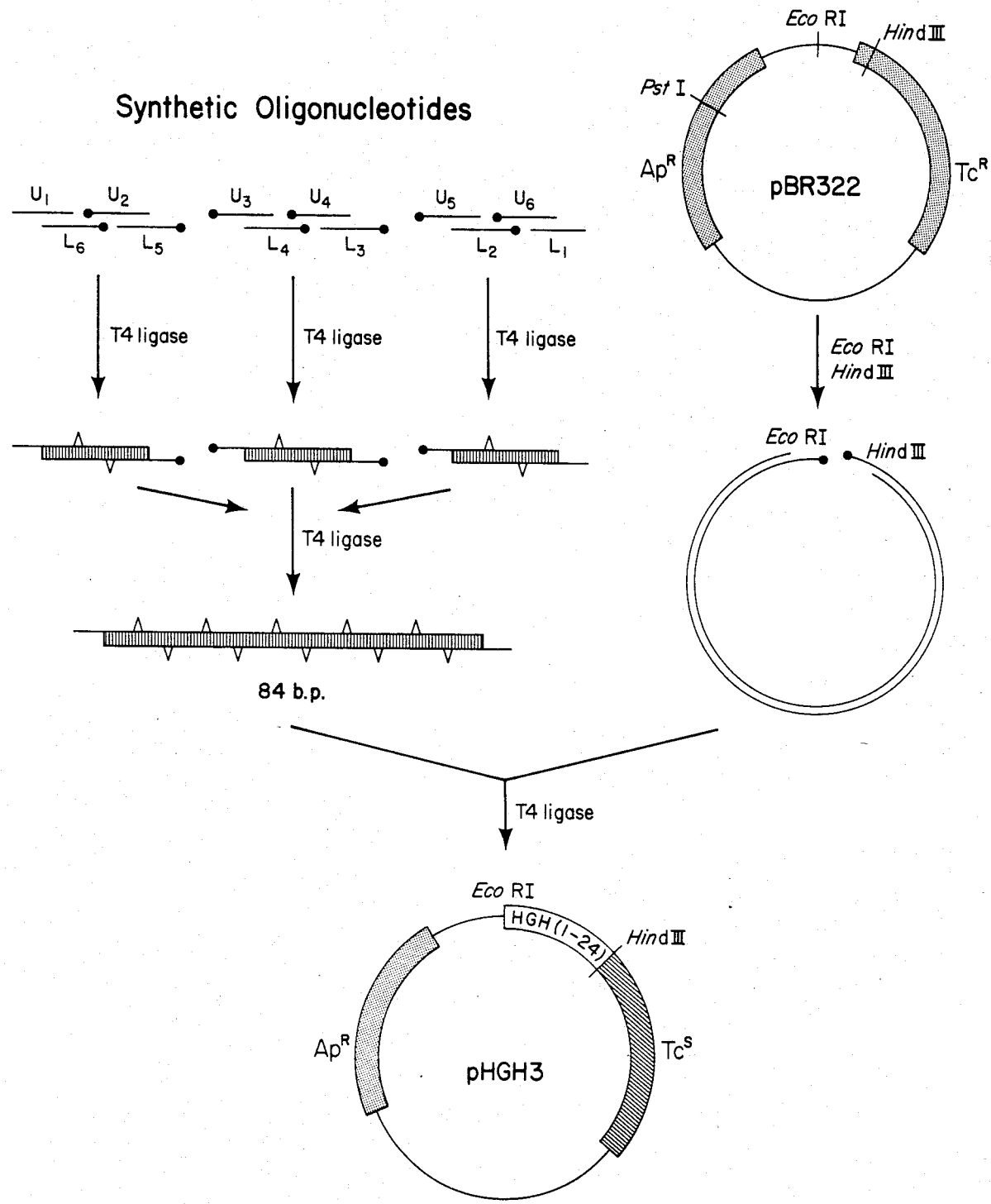
FIG. 2 depicts joinder of the "U" and "L" oligonucleotides to form the gene fragment of FIG. 1, and its insertion in a plasmid cloning vehicle.
Figure 4:
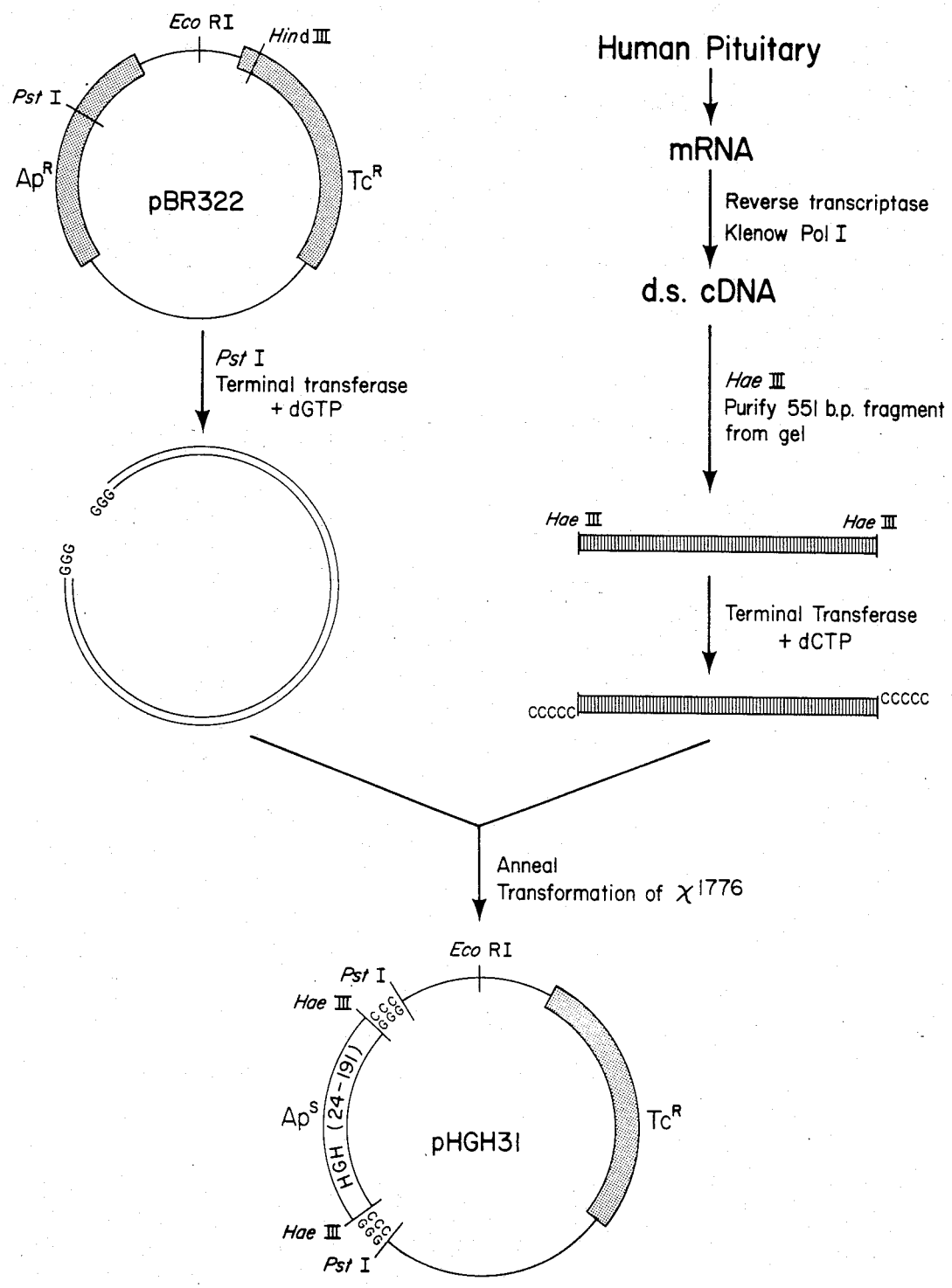
Figure 5:
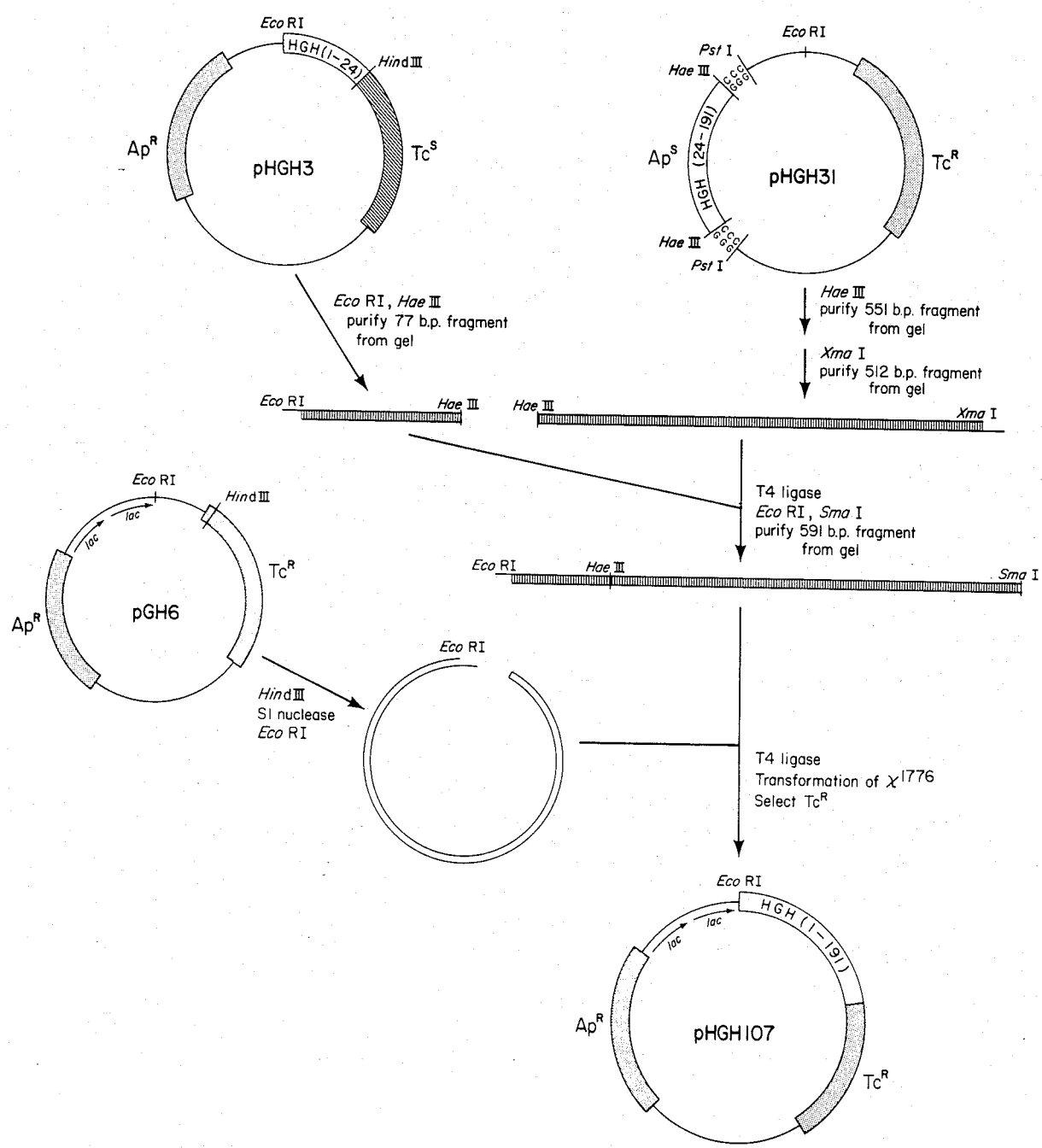

FIG. 4 illustrates the construction of a cloning vehicle for a gene fragment coding for the amino acids of human growth hormone not synthetically derived, and the construction of that gene fragment as complementary DNA by reverse transcription from mRNA isolated from a human pituitary source; and FIG. 5 illustrates the construction of a plasmid capable, in bacteria, of expressing human growth hormone, beginning with the plasmids of FIGS. 2 and 4.

DETAILED DESCRIPTION OF THE INVENTION

The general approach of the invention involves the combination in a single cloning vehicle of plural gene fragments which in combination code for expression of the desired product. Of these, at least one is a cDNA fragment derived by reverse transcription from mRNA isolated from tissue, as by the method of A. Ullrich et al, *Science* 196, 1313 (1977). The cDNA provides a substantial portion, and preferably at least a majority, of the codons for the desired product, while remaining portions of the gene are supplied synthetically. The synthetic and mRNA transcript fragments are cloned separately to provide ample quantities for use in the later combination step.

A variety of considerations influence distribution of codons for the end product as between synthetic and cDNA, most particularly the DNA sequence of complementary DNA determined as by the method of Maxam and Gilbert, *Proc. Nat'l Acad. Sci. USA* 74, 560 (1977). Complementary DNA obtained by reverse transcription will invariably contain codons for at least a carboxy terminal portion of the desired product, as well as other codons for untranslated mRNA downstream from the translation stop signal(s) adjacent the carboxy terminus. The presence of DNA for untranslated RNA is largely irrelevant, although unduly lengthy sequences of that kind may be removed, as by restriction enzyme cleavage, to conserve cellular resources employed in replicating and expressing the DNA for the intended product. In particular cases, the cDNA will contain codons for the entire amino acid sequence desired, as well as extraneous codons upstream from the amino terminus of the intended product. For example, many if not all polypeptide hormones are expressed in precursor form with leader or signal sequences of protein involved, e.g., in transport to the cellular membrane. In expression from eukaryotic cells, these sequences are enzymatically removed, such that the hormone enters the periplasmic space in its free, bioactive form. However, microbial cells cannot be relied upon to perform that function, and it is accordingly desirable to remove sequences coding for such signals or leader sequences from the mRNA transcript. In the course of that removal process the translation start signal is also lost, and almost invariably some codons for the intended product will be removed as well. The synthetic component of the quasi-synthetic gene product of the invention returns these latter codons, as well as supplying anew a translation start signal where the vehicle into which the hybrid gene will ultimately be deployed itself lacks a properly positioned start.

Elimination of the leader sequence from pregrowth hormone cDNA is advantaged by the availability of a restriction site within the growth hormone-encoding portion of the gene. The invention may nevertheless be practiced without regard to the availability of such a site, or in any event without regard to the availability of a restriction site sufficiently near the amino terminus of the desired polypeptide as to obviate the need for extensive synthesis of the gene component not derived from mRNA. Thus, in any cDNA coding for the desired polypeptide and a leader or other bioinactivating sequence the boundary between the latter's codons and those of the mature polypeptide will appear from the amino acid sequence of the mature polypeptide. One may simply digest into the gene coding of the peptide of choice, removing the unwanted leader or other sequence. Thus, for example, given cDNA such as:

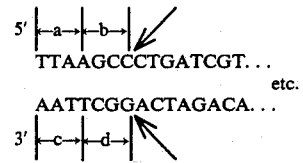

where the endpoint of digestion is indicated by arrow, reaction conditions for exonuclease digestion may be chosen to remove the upper sequences "a" and "b", whereafter S1 nuclease digestion will automatically eliminate the lower sequences "c" and "d". Alternatively and more precisely, one may employ DNA polymerase digestion in the presence of deoxynucleotide triphosphates ("d(A,T,C,G)TP"). Thus, in the foregoing example, DNA polymerase in the presence of dGTP will remove sequence "c" (then stop at "G"), S1 nuclease will then digest "a"; DNA polymerase in the presence of dTTP will remove "d", (then stop at "T") and S1 nuclease will then excise "b", and so on. See generally A. Kornberg, *DNA Synthesis*, pp. 87–88, W. H. Freeman and Co., San Franciso (1974).

More preferably, one may simply construct a restriction site at a convenient point within the portion of the cDNA coding for the desired product, by an application of the mismatch repair synthesis technique of A. Razin et al, *Proc. Nat'l Acad. Sci. USA* 75, 4268 (1978). By this technique one or more bases may be substituted in an existing DNA sequence, using primers containing the mismatched substituent. At least seven palindromic 4-base pair sequences are uniquely recognized by known restriction enzymes, i.e., AGCT (Alu I), CCGG (Hpa II), CGCG (Tha I), GATC (Sau 3A), GCGC (Hha), GGCC (Hae III), and TCGA (Taq I). Where the cDNA sequence contains a sequence differing from one such site in a single base, as statistically is highly likely, repair synthesis will yield replicate cDNA containing the proper, substituent base and hence the desired restriction site. Cleavage will delete DNA for the unwanted leader, after which synthesis will replace codons required for expression of the complete polypeptide. E.g.,:

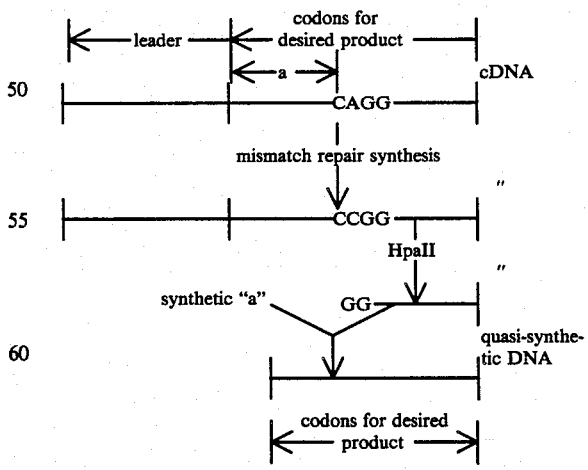

It will be appreciated, of course, that longer restriction sites may be likewise inserted where desired, or that successive repairs may create 4-base pair restriction sites where only two bases common to the site appear at the desired point, etc.

Applications will appear in which it is desirable to express not only the amino acid sequence of the intended product, but also a measure of extraneous but specifically engineered protein. Four such applications may be mentioned by way of example. First, the quasi-synthetic gene may represent a hapten or other immunological determinant upon which immunogenicity is conferred by conjugation to additional protein, such that vaccines are produced. See generally, G.B. patent specification No. 2 008 123A. Again, it may be desirable for biosafety reasons to express the intended product as a conjugate with other, bio-inactivating protein so designed as to permit extracellular cleavage to yield the active form. Third, applications will be presented in which transport signal polypeptides will precede the desired product, to permit production of the same by excretion through the cell membrane, so long as the signal peptide can then be cleaved. Finally, extraneous conjugate designed to permit specific cleavage extracellularly may be employed to compartmentalize intended products otherwise susceptible to degradation by proteases endogenous to the microbial host. At least in the latter three applications, the synthetic adaptor molecular employed to complete the coding sequence of the mRNA transcript can additionally incorporate codons for amino acid sequences specifically cleavable, as by enzymatic action. For example, trypsin will cleave specifically at arg-arg or lys-lys, etc. See GB No. 2 008 123A, supra.

From the foregoing, it will be seen that in its broadest aspect the invention admits of manifold applications, each having in common these attributes:

- a mRNA transcript is employed which codes for a substantial portion of the intended polypeptide's amino acid sequence but which, if expressed alone, would produce a different polypeptide either smaller or larger than the intended product;
- protein-encoding codons for amino acid sequences other than those contained in the intended product, if any, are removed;
- organic synthesis yields fragment(s) coding for the remainder of the desired sequence; and
- the mRNA transcript and synthetic fragment(s) are combined and disposed in a promoter-containing cloning vehicle for replication and expression of either the intended product absent extraneous conjugated protein, or intended product conjugated to but specifically cleavable from extraneous protein.

Of course, the expression product will in every case commence with the amino acid coded for by the translation start signal (in the case of ATG, f-methionine). One can expect this to be removed intracellularly, or in any event to leave the bioactivity of the ultimate product essentially unaffected.

Although it provides a method of general applicability in the production of useful proteins, including antibodies, enzymes and the like, the invention is particularly suited to the expression of mammalian polypeptide hormones and other substances having medical applications, e.g. glucagon, gastrointestinal inhibitory polypeptide, pancreatic polypeptide, adrenocorticotropin, beta-endorphins, interferon, urokinase, blood clotting factors, human albumin, and so on. A preferred embodiment illustrative of the invention is next discussed, in which a quasi-synthetic gene coding for human growth hormone is constructed, cloned and microbially expressed.

CONSTRUCTION AND EXPRESSION OF A CLONING VEHICLE FOR HUMAN GROWTH HORMONE

1. Cloning the Hae III fragment of the mRNA transcript (FIGS. 3 and 4)

Polyadenylated mRNA for human growth hormone (HGH) was prepared from pituitary growth hormone-producing tissue by the procedure of A. Ullrich et al. *Science* 196, 1313 (1977) 1.5 $\mu$g of double strand ("ds") cDNA was prepared from 5 $\mu$g of this RNA essentially as described by Wickens et al. *J. Biol Chem.* 253 2483 (1978), except that RNA polymerase "Klenow fragment", Klenow, *Proc. Nat'l. Aci. USA.* 65, 168 (1970), was substituted for DNA Polymerase I in the second strand synthesis. The restriction pattern of HGH is such that Hae III restriction sites are present in the 3' non-coding region and in the sequence coding for amino acids 23 and 24 of HGH, as shown in FIG. 3. Treatment of ds HGH cDNA with Hae III gives a DNA fragment of 551 base pairs ("bp") coding for amino acids 24-191 of HGH. Thus, 90 ng of the cDNA was treated with Hae III, electrophoresed on an 8% polyacrylamide gel, and the region at 550 bp eluted. Approximately 1 ng of cDNA was obtained.

pBR322 prepared as in F. Bolivar et al., *Gene* 2 (1977) 95-113 was chosen as the cloning vehicle for the cDNA. pBR322 has been fully characterized, J. G. Sutcliffe, *Cold Spring Harbor Symposium* 43, 70 (1978), is a multicopy replicating plasmid which exhibits both ampicillin and tetracycline resistance owing to its inclusion of the corresponding genes ("Ap$^R$" and "Tc$^R$", respectively, in FIG. 4), and which contains recognition sites for the restriction enzymes Pst I, EcoRI and Hind III as shown in the Figure.

The GC tailing method of Chang, A. C. Y. et al. *Nature* 275 617 (1978) was employed to combine the products of Pst I cleavage of pBR322 and of Hae III digestion of the mRNA transcript, inserting the cDNA fragment into the Pst I site of pBR322 in such manner as to restore the Hae III restriction sites (GG $\downarrow$ CC) on the cDNA while restoring the Pst I restriction sites (CTGCA $\downarrow$ G) at each end of the insert.

Thus, terminal deoxynucleotidyl transferase (TdT) was used to add approximately 20 dC residues per 3' terminus as described previously, Chang, A. Y. C., supra. 60 ng of Pst I-treated pBR322 as tailed similarly with about 10 dG residues per 3' terminus. Annealing of the dC-tailed ds cDNA with the dG-tailed vector DNA was performed in 130 $\mu$l of 10 mM Tris-HCl (pH 7.5), 100 mM NaCl, 0.25 mM EDTA. The mixture was heated to 70° C., allowed to cool slowly to 37° C. (12 hours), then to 20° C. (6 hours) before being used to transform *E. Coli.* x1776. DNA sequence analysis of the plasmid pHGH31 cloned in x1776 by the method of Maxam and Gilbert, *Proc. Nat'l. Acad. Sci. USA* 74, 560 (1977) resulted in confirmation of the codons for amino acids 24-191 of HGH, as shown in FIG. 3.

*E. Coli* K-12 strain x1776 has the genotype F$^-$ tonA53 dapD8 minA1 supE42 $\Delta$40[gal-uvrB] $\lambda^-$ minB2 rfb-2 nalA25 oms-2 thyA57* metC65 oms-1 $\Delta$29 [bioH-asd] cycB2 cycA1 hsdR2. x1776 has been certified by the National Institutes of Health as an EK2 host vector system.

x1776 has an obligate requirement for diaminopimelic acid (DAP) and cannot synthesize the mucopolysaccharide colanic acid. It thus undergoes DAP-less death in all environments where DAP is limiting but sufficient nutrients exist to support cellular metabolism and growth. It requires thymine or thymidine and undergoes thymineless death with degradation of DNA when thymine and thymidine are absent from the environment but when sufficient nutrients are present to sustain metabolic activity. x1776 is extremely sensitive to bile and thus is unable to survive and thus is unable to survive passage through the intestinal tract of rats. x1776 is extremely sensitive to detergents, antibiotics, drugs and chemicals. x1776 is unable to carry out either dark or photo repair of UV-induced damage and is thus several orders of magnitude more sensitive to sunlight than wild-type strains of E. Coli. x1776 is resistant to many transducing phages and is conjugation deficient for inheritance of many different types of conjugative plasmids due to the presence of various mutations. x1776 is resistant to nalidixic acid, cycloserine and trimethoprim. These drugs can therefore be added to media to permit monitoring of the strain and to preclude transformation of contaminants during transformation.

x1776 grows with a generation time of about 50 min. in either L broth of Penassay broth when supplemented with 100 μg DAP/ml and 4 μg thymidine/ml and reaches final densities of $8-10 \times 10^8$ cells/ml at stationary phase. Gentle agitation by swirling and shaking back and forth for a period of 1-2 min. adequately suspends cells with maintenance of 100% viability. Additional details concerning x1776 appear in R. Curtis et al., *Molecular Cloning of Recombinant DNA*, 99-177, Scott and Werner, eds., Academic Press (N.Y. 1977).

2. Construction and Cloning of the Synthetic Gene Fragment (FIGS. 1 and 2)

The strategy for construction of the HGH quasi-synthetic gene included construction of a synthetic fragment comprising a blunt-end restriction cleavage site adjacent the point at which the fragment would be joined to the mRNA transcript. Thus, as shown in FIG. 1, the synthetic gene for the first 24 amino acids of HGH contained a Hae III cleavage site following amino acid 23. The distal end of the synthetic fragment was provided with a "linker" that permitted annealing to a single strand terminal resulting from restriction cleavage in the plasmid in which the mRNA transcript and synthetic fragment would ultmately be joined.

As shown in FIG. 1, the 5' ends of the duplex fragment have single stranded cohesive termini for the Eco RI and Hind III restriction endonucleases to facilitate plasmid construction. The methionine codon at the left end provides a site for initiation of translation. Twelve different oligonucleotides, varying in size from undecamer to hexadecamer, were synthesized by the improved phosphotriester method of Crea, R. *Proc. Nat'l. Acad. Sci. USA* 75, 5765 (1978). These oligonucleotides, $U_1$ to $U_6$ and $L_1$ to $L_6$ are indicated by arrows.

10 μg amounts of $U_2$ through $U_6$ and $L_2$ through $L_6$ were phosphorylated using $T_4$ polynucleotide kinase and $(\gamma^{32}$-P)ATP by a published procedure. Goeddel, D. V. et al. *Proc. Nat'l. Acad. Sci. USA* 76, 106 (1979).

Three separate $T_4$ ligase catalyzed reactions were performed: 10 μg of 5'-OH fragment $U_1$ was combined with the phosphorylated $U_2$, $L_5$ and $L_6$; phosphorylated $U_3$, $U_4$, $L_3$ and $L_4$ were combined; and 10 μg of 5'-OH fragment $L_1$ was combined with the phosphorylated $L_2$, $U_5$ and $U_6$. These ligations were carried out at 4° C. for 6 hours in 300 μl of 20 mM Tris-HCl (pH 7.5), 10 mM MgCl$_2$, 10 mM dithiothreitol, 0.5 mM ATP using 20 units of $T_4$ ligase. The three ligation mixtures were then combined, 20 units $T_4$ ligase added, and the reaction allowed to proceed for 12 hours at 20° C. The mixture was ethanol precipitated and electrophoresed on a 10% polyacrylamide gel. The band migrating at 84 base pairs was sliced from the gel and eluted. pBR322 (1 μg) was treated with Eco RI and Hind III, the large fragment isolated by gel electrophoresis and ligated to the synthetic DNA. This mixture was used to transform *E. Coli.* K-12 strain 294 (end A, thi−, hsr−, hsm$_k$+). Strain 294 was deposited Oct. 30, 1978 in the American Type Culture Collection (ATCC No. 31446), without restriction. Sequence analysis by the Maxam and Gilbert technique, supra, on the Eco RI-Hind III insert from a plasmid pHGH3 of one transformant confirmed that depicted in FIG. 1.

3. Construction of Plasmid for the Bacterial Expression of HGH (FIG. 5)

With the synthetic fragment in pHGH3 and the mRNA transcript in pHGH31, a replicable plasmid containing both fragments was constructed using the expression plasmid pGH6, as shown in FIG. 5. The expression plasmid, which contains tandem lac promoters, was first constructed as follows. A 285 base pair Eco RI fragment containing two 95 base pair UV5 lac promoter fragments separated by a 95 base pair heterlogous DNA fragent was isolated from plasmid pKB268, K. Backman, et al., *Cell,* Vol. 13, 65–71 (1978). The 285 bp fragment was inserted into the Eco RI site of pBR322 and a clone pGH1 isolated with the promoters oriented toward and in proper reading phase with the gene for tetracycline resistance. The Eco RI site distal to the latter gene was destroyed by partial Eco RI digestion, repair of the resulting single stranded Eco RI ends with DNA polymerase I and recirculatization of the plasmid by blunt-end ligation. The resulting plasmid, pGH6, contains a single Eco RI site properly positioned with respect to the promoter system into which the completed gene for HGH could be inserted.

To ready the synthetic fragment for combination with the RNA transcript, 10 μg of pHGH3 was cleaved with Eco RI and Hae III restriction endonucleases and the 77 base pair fragment containing coding sequences for HGH amino acids 1-23 was isolated from an 8% polyacrylamide gel.

The plasmid pHGH 31 (5 μg) was next cleaved with Hae III. The 551 bp HGH sequence and a comigrating 540 bp Hae III fragment of pBR322 were purified by gel electrophoresis. Subsequent treatment with Xma I cleaved only the HGH sequence, removing 39 base pairs from the 3' noncoding region. The resulting 512 bp fragment was separated from the 540 bp pBR322 Hae III piece by electrophoresis on a 6% polyacrylamide gel. 0.3 μg of the 77 bp Eco RI-Hae III fragment was polymerized with $T_4$ ligase in a 16 μl reaction vessel for 14 hours at 4° C. The mixture was heated to 70° C. for 5' to inactivate the ligase, then treated with Eco RI (to cleave fragments which had dimerized through their Eco RI sites) and with Sma I (to cleave Xma I dimers), yielding a 591 bp fragment with an Eco RI "cohesive" end and a Sma I "blunt" end. After purification on a 6% polyacrylamide gel, approximately 30 ng of this fragment were obtained. It should be noted that the expression plasmid pGH6 contains no Xma I recognition site. However, Sma I recognizes the same site as Xma I, but cuts through the middle of it, yielding blunt ends. The Sma-cleaved terminus of the fragment derived from gHGH 31 can accordingly be blunt end ligated into pGH6.

The expression plasmid pGH6, containing tandem lac UV5 promoters, was treated successively with Hind III, nuclease S1, and Eco RI and purified by gel electrophoresis. 50 ng of the resulting vector, which had one Eco RI cohesive end and one blunt end was ligated to 10 ng of the 591 bp HGH DNA. The ligation mixture was used to transform *E. Coli.* X1776. Colonies were selected for growth on tetracycline (12.5 μg/ml). It is noteworthy that insertion of the hybrid HGH gene into pGH6 destroys the promoter for the tetracycline resistance gene, but that the tandem lac promoter permits read-through of the structural gene for tet resistance, retaining this selection characteristic. Approximately 400 transformants were obtained. Filter hybridization by the Grunstein-Hogness procedure, *Proc. Nat'l. Acad. Sci. USA,* 72, 3961 (1975) identified 12 colonies containing HGH sequences. The plasmids isolated from three of these colonies gave the expected restriction patterns when cleaved with Hae III, Pvu II, and Pst I. The DNA sequence of one clone, pHGH107, was determined.

Human growth hormone expressed by the transformants was easily detected by direct radioimmunoassay performed on serial dilutions of lysed cell supernatants using the Phadebas HGH PRIST kit (Pharmacia).

To demonstrate that HGH expression is under the control of the lac promoter, p HGH107 was transformed into *E. Coli* strain D1210 a lac+(i$^Q$O+z+y+), a lac repressor overproducer. Meaningful levels of HGH expression could not be detected until addition of the inducer IPTG (isopropylthiogalactoside).

Removal of the Eco RI site in pHGH107 would leave the ATG start signal the same distance from the ribosome binding site codons of the lac promoter as occurs in nature between those codons and the start signal for β-galactosidase. To determine whether expression would be increased by mimicking this natural spacing we converted pHGH 107 to pHGH 107-1 by opening the former with Eco RI, digesting the resulting single strand ends with S1 endonuclease, and recircularizing by blunt-end ligation with T4 ligase. Although the resulting plasmid proved likewise capable of expressing HGH, it surprisingly did so to a lesser extent than did pGH107, as shown by direct radioimmunoassay.

It will be apparent to those skilled in the art that the present invention is not limited to the preferred embodiment just discussed, but rather only to the lawful scope of the appended claims. Variations other than those hitherto discussed will be apparent, whether in the choice of promoter system, parental plasmid, intended polypeptide product or elsewhere. For example, other promoter systems applicable to the present invention include the lambda promoter, the arabinose operon (phi 80 d ara) or the colicin E1, galactose, alkaline phosphatase or tryptophan promoter systems. Host organisms for bacterial expression may be chosen, e.g., from among the Enterobacteriaceae, such as strains of *Escherichia coli* and Salmonella; Bacillaceae, such as bacillus subtilis; Pneumococcus; Streptococcus; and Haemophilus influenzae. Of course, the choice of organism will control the levels of physical containment in cloning and expression that should be practiced to comply with National Institutes of Health Guidelines for Recombinant DNA, 43 Fed. Reg. 60,080 (1978).

While preferred for bench-scale practice of the present invention, *E. Coli.* x1776 could prove of limited practicality in large-scale industrial manufacture owing to the debilitations purposefully incorporated in it for biosafety reasons. With appropriate levels of physical, rather than biological, containment such organisms as *E. Coli.* K-12 strain 294, supra. and *E. Coli.* strain RR1, genotype: Pro$^-$Leu$^-$Thi$^-$R$_B^-$recA+Str$^r$ Lac y$^-$ could be employed in larger scale operation. *E. Coli.* RR1 is derived from *E. Coli* HB101 (H. W. Boyer, et al, *J. Mol. Bio.* (1969) 41 459–472) by mating with *E. Coli.* K12 strain KL16 as the Hfr donor. See J. H. Miller, *Experiments in Molecular Genetics* (Cold Spring Harbor, N.Y., 1972). A culture of *E. Coli.* RR1 was deposited Oct. 30, 1978 with the American Type Culture Collection, without restriction as to access (ATCC No. 31343). A culture of x1776 was similarly deposited July 3, 1979 in the American Type Culture Collection (ATCC No. 31537). Deposits of the following were made in the American Type Culture Collection July 3, 1979: plasmid pHGH107 (ATCC No. 40011); plasmid pGH6 (ATCC No. 40012); strain x1776 transformed with pHGH107 (ATCC No. 31538) and *E. Coli* K12 strain 294 transformed with pGH6 (ATCC No. 31539).

Organisms produced according to the invention may be employed in industrial scale fermentative production of human growth hormone, yielding product in quantities and for applications hitherto unattainable. For example, transformant *E. Coli* cultures may be grown up in aqueous media in a steel or other fermentation vessel conventionally aerated and agitated, in aqueous media at, e.g., about 37° C. and near neutral pH (e.g., pH 7±0.3) supplied with appropriate nutriments such as carbohydrate or glycerol, nitrogen sources such as ammonium sulfate, potassium sources such as potassium phosphate, trace elements, magnesium sulfate and the like. Transformant organisms preferably exhibit one or more selection characteristics, such as antibiotic resistance, so that selection pressures may be imposed to discourage competitive growth of wild-type *E. coli.* As an example, in the case of an ampicillin or tetracycline-reistant organism the antibiotic may be added to the fermentation medium to select out wild-type organisms which lack the resistance characteristic.

Upon completion of fermentation the bacterial suspension is centrifuged or the cellular solids otherwise collected from the broth and then lysed by physical or chemical means. Cellular debris is removed from supernatant and soluble growth hormone isolated and purified.

Human growth hormone may be purified from bacterial extracts using one or a combination of (1) polyethyleneimine fractionation; (2) gel filtration chromatography on Sephacryl S-200; (3) ion exchange chromatography on Biorex-70 resin or CM Sephadex; (4) ammonium sulphate and/or pH fractionation; and (5) affinity chromatography using antibody resins prepared from anti-HGH IgG isolated from immunosensitized animals or hybridomas; and desorbed under acid or slightly denaturing conditions.

We claim:

1. A replicable bacterial plasmid which, in a transformant bacterium, will express a gene for human growth hormone unaccompanied by the human growth hormone leader sequence or other extraneous protein bound thereto.

2. A plasmid according to claim 1 whose human growth hormone-encoding gene comprises in substantial proportion cDNA or a replication thereof.

3. A plasmid according to claim 2 which exhibits resistance to at least one antibiotic.

4. A plasmid according to claim 3 which lacks the tet promoter yet exhibits tetracycline resistance.

5. A plasmid according to claim 4 in which the human growth hormone-encoding gene is under the control of tandem lac promoters.

6. The plasmid pHGH107.

7. The plasmid pHGH107-1.

* * * * *